US009981121B2

(12) United States Patent
Seifert et al.

(10) Patent No.: US 9,981,121 B2
(45) Date of Patent: May 29, 2018

(54) IMPLANTABLE MEDICAL DEVICES, SYSTEMS AND COMPONENTS THEREOF

(71) Applicant: Medtronic, Inc., Minneapolis, MN (US)

(72) Inventors: Kevin R. Seifert, Forest Lake, MN (US); Nathan L. Olson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 736 days.

(21) Appl. No.: 14/283,278

(22) Filed: May 21, 2014

(65) Prior Publication Data

US 2015/0306374 A1 Oct. 29, 2015

Related U.S. Application Data

(60) Provisional application No. 61/984,900, filed on Apr. 28, 2014.

(51) Int. Cl.
*A61N 1/05* (2006.01)
*A61M 25/00* (2006.01)
*A61M 25/04* (2006.01)

(52) U.S. Cl.
CPC .......... *A61N 1/05* (2013.01); *A61M 25/0043* (2013.01); *A61M 25/04* (2013.01)

(58) Field of Classification Search
CPC .................................. A61N 1/05; A61N 1/057
(Continued)

(56) References Cited

U.S. PATENT DOCUMENTS 3,123,077 A 3/1964 Alcamo
5,476,493 A 12/1995 Muff
(Continued)

FOREIGN PATENT DOCUMENTS

WO 2004028621 4/2004
WO 2005077451 8/2005
(Continued)

OTHER PUBLICATIONS (PCT/US2015/025864) PCT Notification of Transmittal of the International Search Report and the Written Opinion of the International Searching Authority, dated Jul. 7, 2015, 11 pages.
(Continued)

*Primary Examiner* — Nadia A Mahmood

(57) ABSTRACT

An implantable medical therapy delivery device includes a non-conductive filament extending along a length of an outer surface of an insulative body of the device, wherein the filament includes a plurality of fixation projections and is secured to the outer surface of the insulative body such that the projections protrude outward from the outer surface and are spaced apart from one another along the length of the outer surface. The filament may be wound about the length with an open pitch. In some cases, the insulative body includes an open-work member forming at least a portion of the outer surface thereof, and the filament may be interlaced with the open-work member. In these cases, the filament may be bioabsorbable, for example, to provide only acute fixation via the projections thereof, while the open-work member provides a structure for tissue ingrowth and, thus, more permanent or chronic fixation.

20 Claims, 6 Drawing Sheets

(58) Field of Classification Search
USPC .................................................. 607/116, 129
See application file for complete search history.

(56) References Cited

U.S. PATENT DOCUMENTS

| | | | |
|---|---|---|---|
| 5,984,896 A | 11/1999 | Boyd | |
| 7,021,086 B2 | 4/2006 | Ory et al. | |
| 7,212,869 B2 | 5/2007 | Wahlstrom et al. | |
| 7,270,669 B1 | 9/2007 | Sra | |
| 7,319,905 B1* | 1/2008 | Morgan | A61N 1/0587 607/129 |
| 8,086,324 B1 | 12/2011 | Vase | |
| 8,246,652 B2 | 8/2012 | Ruff | |
| 8,353,931 B2 | 1/2013 | Stopek et al. | |
| 2002/0035331 A1 | 3/2002 | Brockway et al. | |
| 2003/0105501 A1 | 6/2003 | Warman et al. | |
| 2004/0039415 A1* | 2/2004 | Zamierowski | A61B 17/064 606/215 |
| 2004/0230279 A1 | 11/2004 | Cates et al. | |
| 2005/0033394 A1 | 2/2005 | Seifert et al. | |
| 2007/0239244 A1 | 10/2007 | Morgan et al. | |
| 2008/0009914 A1 | 1/2008 | Buysman et al. | |
| 2008/0077220 A1 | 3/2008 | Reddy | |
| 2010/0152798 A1 | 6/2010 | Sanghera et al. | |
| 2011/0009935 A1 | 1/2011 | Kane et al. | |
| 2011/0130774 A1 | 6/2011 | Criscuolo et al. | |
| 2012/0029335 A1 | 2/2012 | Sudam et al. | |
| 2012/0046515 A1 | 2/2012 | Woo et al. | |
| 2012/0316627 A1 | 12/2012 | Finlay et al. | |
| 2013/0030511 A1 | 1/2013 | Bardy et al. | |
| 2014/0025094 A1 | 1/2014 | Glick et al. | |

FOREIGN PATENT DOCUMENTS

| | | |
|---|---|---|
| WO | 2008094952 | 8/2008 |
| WO | 13025678 A1 | 2/2013 |
| WO | 13049787 A1 | 4/2013 |

OTHER PUBLICATIONS

ProGrip™ Laparascopic Self-Fixating Mesh—Value Analysis Committee—Product Information Kit, COVIDIEN, 23 pages, COVIDIEN with logo, COVIDIEN logo and positive results for life are U.S. and internationally registered trademarks of COVIDIEN AG.™* Trademark of its respective owner. Other brands are trademarks of a Covidien company. © 2013 Covidien 1.13 M130037.

Quill™ Knotless Tissue-Closure Device Product Catalog, 12 pages. QuillDevice.com; Quill 0104R6 11/13 QUILL™ and MONODERM™ are trademarks of Surgical Specialties Corporation. © 2007-2013 Surgical Specialties Corporation.

V-Loc™ Wound Closure Devices Product Overview, 2 pages, COVIDIEN, COVIDIEN with logo, Covidien logo and positive results for life are U.S.and/or internationally registered trademarks of Covidien AG. Other brands are trademarks of a Covidien company. © 2011 Covidien. 11.11 P100049.

* cited by examiner

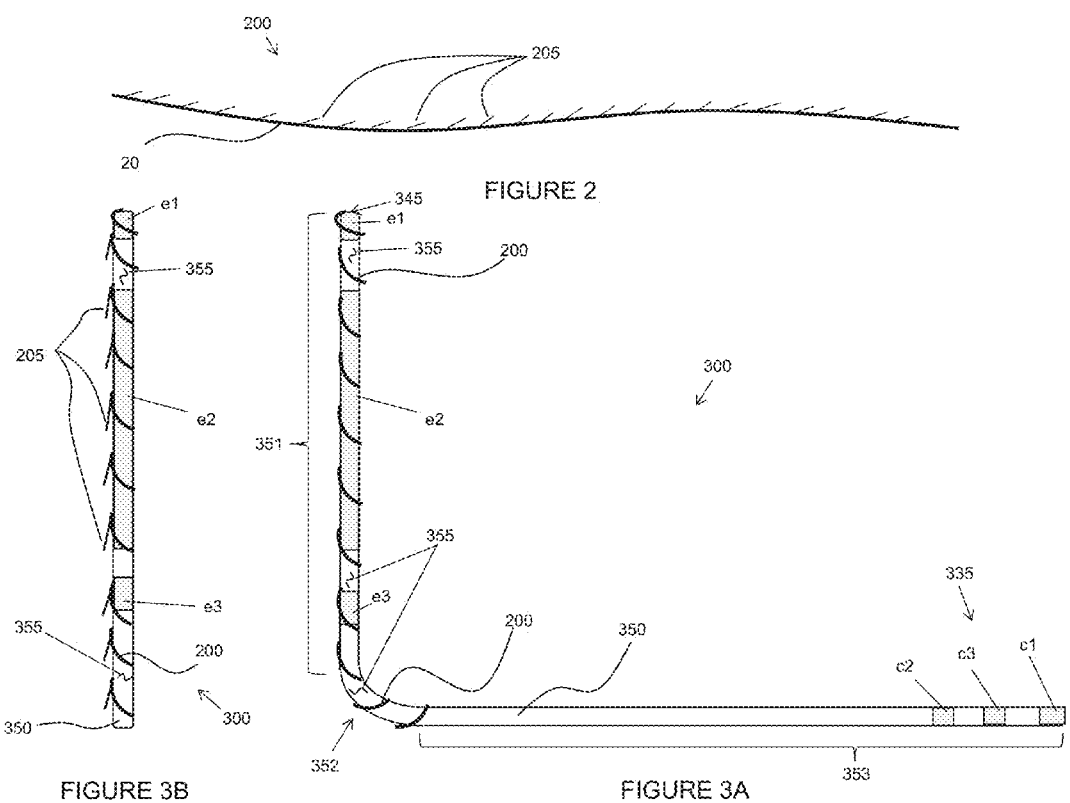

IMPLANTABLE MEDICAL DEVICES, SYSTEMS AND COMPONENTS THEREOF

FIELD OF THE DISCLOSURE

The present disclosure pertains to implantable medical systems, and more particularly to implantable medical therapy delivery devices, such as electrical stimulation leads or drug delivery catheters, and fixation components thereof.

BACKGROUND

An implantable medical system that provides therapy, for example, cardiac or neurological therapy, often includes an elongate insulative body configured to extend within a patient's body to a target site and to deliver a therapy to the target site. The therapy may be electrical stimulation therapy, drug therapy (e.g., delivery of a therapeutic agent), other therapy or a combination of therapies.

SUMMARY

Embodiments of implantable therapy delivery devices, such as electrical stimulation leads or drug delivery catheters are disclosed herein. According to one embodiment, an implantable therapy delivery device includes an elongate insulative body having an outer surface and a non-conductive filament extending along a length of the outer surface of an insulative body of the device. The filament includes a plurality of fixation projections and is secured to the outer surface of the insulative body such that at least a portion of the plurality of projections protrude outward from the outer surface and are spaced apart from one another along the length of the outer surface.

The filament may be wound about the length with an open pitch, and/or, in some embodiments, the filament is interlaced with an open-work member that forms at least a portion of the length of the outer surface of the insulative body. According to some embodiments, the open-work member may overlap one or more electrodes of at least one electrode circuit of the device, and, in some cases, may further form another length of the outer surface of the insulative body that extends proximally from the secured filament.

According to another embodiment, an implantable medical device system comprises an implantable stimulation device and an implantable stimulation lead, the device and lead being adapted for coupling to one another. The stimulation lead includes an elongate insulative body including a proximal segment, a distal segment, and a pre-formed bend extending therebetween, a stimulation electrode circuit, at least one sense electrode circuit. The stimulation and sense electrode circuits being supported by the insulative body, the distal segment of the insulative body having electrodes of the stimulation electrode circuit and the at least one sense electrode circuit mounted thereabout. The stimulation lead also includes a non-conductive filament including a plurality of fixation projections and extending along a length of an outer surface of the pre-formed bend and distal segment of the insulative body, the filament being wound about all or a portion of the length with an open pitch and being secured to the outer surface such that the projections thereof protrude outward from the outer surface and are spaced apart from one another along the length of the outer surface.

The insulative body of the lead may further include one or more open-work members to form all or a portion of the length of the outer surface along which the fiber extends, the fiber being interlaced therewith. In some embodiments that include a single open-work member to form the length of the outer surface along which the fiber extends, the open-work member may also form another length of the outer surface of the insulative body that extends proximally from the pre-formed bend.

In those embodiments that include both the non-conductive filament and the open-work member, the filament may be bioabsorbable, for example, to provide only acute fixation via the projections thereof, while the open-work member provides a structure for tissue ingrowth and, thus, more permanent or chronic fixation. Some embodiments of components for forming a length of an outer surface of an implantable therapy delivery device include a tubular open-work member and a non-conductive filament interlaced therewith, wherein the filament includes a plurality of fixation projections, at least a portion of which protrude outward from the open-work member.

In another embodiment, the disclosure provides a component for forming a length of an outer surface of an elongate insulative body of an implantable medical lead. The component includes a tubular open-work member and a non-conductive filament including a plurality of fixation projections, the filament being interlaced with the open-work member such that the plurality of projections protrude outward from the open-work member.

Although the disclosed embodiments are described in the context of the above-referenced subcutaneously implantable defibrillation system, it should be understood that embodiments of the present invention are not so limited and may be employed by other types of implantable devices that include elongate insulative bodies, for example, suitable for implantation in other sites of a patient's body, either for the delivery of electrical stimulation or for the delivery of therapeutic drugs.

BRIEF DESCRIPTION OF THE DRAWINGS

The following drawings are illustrative of particular embodiments and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements.

FIG. 2 is a plan view of an exemplary non-conductive filament employed by some embodiments of the present application.

FIGS. 3A-B are a plan view and a corresponding end view of an implantable medical stimulation lead, which may employ the filament shown in FIG. 2.

DETAILED DESCRIPTION

Figure 1:
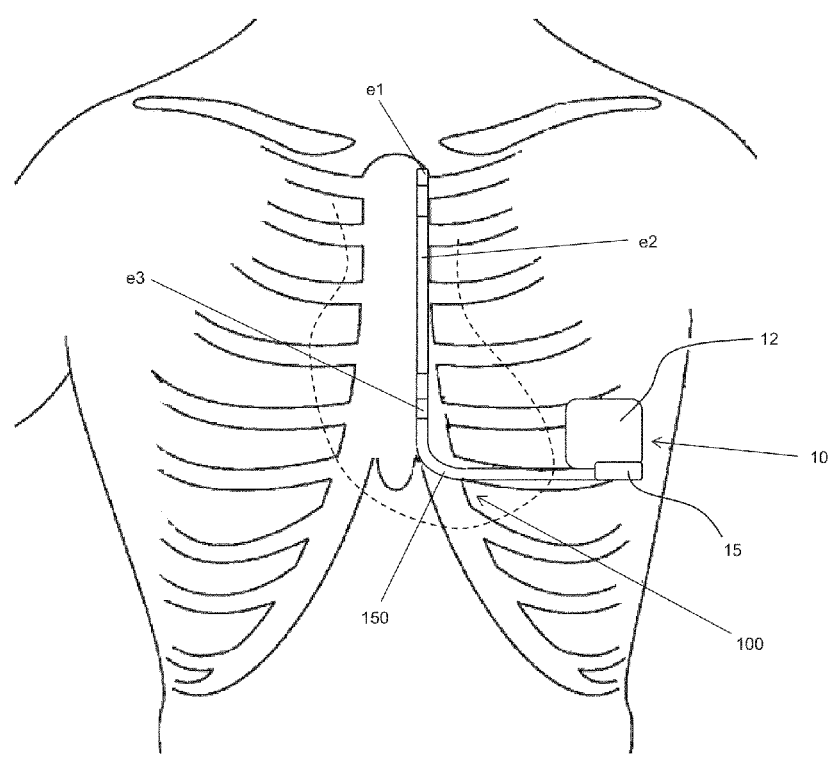
FIG. 1 is a schematic depiction of a patient's torso with ribcage, heart (dashed lines), and an implanted medical system.

FIG. 1 is a schematic depiction of a patient's torso with ribcage, heart (dashed lines), and an example implantable medical system implanted within the patient. The implantable medical system of FIG. 1 is an implantable cardioverter-defibrillator (ICD) system that includes an implantable stimulation lead 100 and an implantable stimulation pulse generator 10 coupled together via a connector module 15 of pulse generator 10. Connector module 15 includes a bore in which electrical contacts are mounted and into which a connector of lead 100 is inserted for coupling with the contacts. The contacts of connector module 15 are coupled, for example, via hermetically sealed feedthrough assemblies, to electronic circuitry and a power source, which are contained in a hermetically sealed housing 12 of pulse generator 10, for example, formed by a titanium shell.

The implanted pulse generator 10 is shown located within a subcutaneous pocket formed in proximity to the patient's left axilla and infra-mammary crease, and the implanted lead 100 is shown extending within a subcutaneously formed tunnel that extends medially above the ribcage from pulse generator 10, into proximity with the sternum, approximately level with the xiphoid, and then superiorly above the sternum and/or ribcage along the left side of the sternum. An implanted medical system in which both the pulse generator 10 and lead 100 are implanted subcutaneously above the ribcage and/or sternum is referred to herein as a subcutaneous system.

Implantable stimulation pulse generator 10 and lead 100 may, however, be implanted at other locations within the patient. For example, in another example, lead 100 may extend medially from pulse generator 10, into proximity with the sternum, approximately level with the xiphoid, and then superiorly underneath/below the sternum and/or ribcage (e.g., on the posterior side of the sternum and/or ribcage) in the substernal space, which includes the anterior mediastinum. An example system including such a substernal lead is described in detail U.S. patent application Ser. No. 14/261,470 filed on Apr. 25, 2014 and titled, "IMPLANTABLE CARDIOVERTER-DEFIBRILLATOR (ICD) SYSTEM INCLUDING SUBSTERNAL LEAD," the content of which is incorporated by reference herein in its entirety. An implanted medical system in which the distal portion of lead 100 is implanted underneath/below the sternum and/or the ribcage is referred to herein as a substernal system.

In the example of FIG. 1 Lead 100 includes two pace/sense electrodes e1, e3 and a defibrillation electrode e2, each of which extends around at least a portion of an outer surface of an elongate insulative body 150 of lead 100, and each of which is part of a corresponding electrode circuit, the elongate conductors and contacts of which cannot be seen. Suitable constructions of electrodes e1, e2, e3, conductors, and contacts for the electrode circuits of lead 100 are well known to those skilled in the art. The illustrated exemplary system is configured to detect cardiac arrhythmias, e.g., ventricular tachycardia (VT) or ventricular fibrillation (VF), via electrodes e1, e3 and the corresponding circuitry contained within pulse generator housing 12, and to treat the detected arrhythmias via one or more high voltage defibrillation or cardioversion shocks delivered by the device circuitry across stimulation electrode e2 and device housing 12, according to methods known in the art. In some instances, the system 10 may further provide pacing therapy (e.g., antitachycardia pacing (ATP) or post-shock pacing) via at least one of electrodes e1, e3 in addition to the high voltage defibrillation or cardioversion shocks.

Those skilled in the art appreciate the importance of fixing the implanted lead 100 at the target site, for example, in order to maintain a stable location of electrodes e1, e2, e3 relative to the heart of the patient, and relative to the implanted pulse generator 10. Likewise, any other type of implantable therapy delivery device that includes an elongate body like lead 100 benefits from stable fixation. Typical subcutaneous fixation methods involve manually suturing portions of delivery devices to the subcutaneous tissue, and these methods may require multiple and/or enlarged incisions to provide adequate access for the suturing process. Lead 100 of FIG. 1 includes a fixation structure that is described in further detail with respect to FIGS. 2-5. As will be described in further detail herein, lead 100 includes a non-conductive filament extending along a length of an outer surface of the insulative body 150 of lead 100 and having a plurality of fixation projections. The filament may be secured to the outer surface of the body such that the projections protrude outward from the outer surface and are spaced apart from one another along the length of the outer surface. Various examples are described with respect to FIGS. 2-5. These fixation structures, components, methods, and/or mechanisms allow for the desired fixation without the burdens described above with respect to typical fixation methods.

The following detailed description is exemplary in nature and is not intended to limit the scope, applicability, or configuration of the disclosure in any way. Rather, the following description provides practical examples, and those skilled in the art will recognize that some of the examples may have suitable alternatives. For example, the fixation structures described herein may be used in conjunction with other implantable medical therapy delivery devices. For example, the fixation structures described herein may be used with electrical stimulation leads used to electrical stimulation therapy to a spine, brain, bladder, or other anatomical location within the body. As another example, the fixation structures described herein may be used with drug delivery catheters that provide a therapeutic agent to a location within the patient.

FIG. 2 is a plan view of an exemplary non-conductive filament 200 employed by some embodiments of the present application, for example, an implantable medical stimulation lead 300, which is shown a plan view and a corresponding end view in FIGS. 3A-B. FIG. 2 illustrates filament 200 including a plurality of fixation projections 205 protruding from an elongate strand portion 20 thereof. Filament 200 may be formed from any suitable biocompatible polymer, such as polyethylene, polyester, nylon, polybutester, Polyether ether ketone, or polypropylene, for example, by extrusion and a subsequent cutting process to form projections 205. According to the illustrated embodiment, strand portion 20 of filament 200 is relatively flexible so that filament 200 can be secured to, and extend along a length of an outer surface 355 of an insulative body 350 of lead 300 to form a fixation feature that does not significantly increase a stiffness of body 350.

According to an exemplary embodiment, strand portion 20 has a diameter between approximately 0.1 mm and approximately 1 mm, wherein each fixation projection 205 is barb-like and has a length between approximately 0.004 inch and approximately 0.080 inch, and projections 205 are spaced apart, along a length of filament 200, for example, by a distance of between approximately 0.005 inch and approximately 0.5 inch. FIG. 2 illustrates all of projections 205 extending in the same direction from strand 20, but in alternate embodiments projections 205 may extend in different directions. In any case, when filament 200 is employed as a fixation feature, for example, as illustrated in FIGS. 3A-B, being secured to outer surface 355 of insulative body 350, a significant number of projections 205 protrude outward from outer surface 355 in order to engage with surrounding subcutaneous or substernal tissue and/or muscle. In one example, a significant number of projections 205 may engage with surrounding subcutaneous tissue in the above described subcutaneously formed tunnel shown in FIG. 1, when lead 300 is implanted with device 10, in lieu of lead 100. FIG. 3B illustrates a distal segment 351 of lead 300 with filament 200 secured to outer surface 355 such that projections 205 are all directed to the left hand side of FIG. 3B, which corresponds to a direction into the page of FIGS. 1 and 3A. Such a direction may be preferred for the engagement of projections 205 into fascia of the patient, when lead 300 extends between the fascia and adipose tissue; however, in alternate embodiments, filament 200 may be secured to outer surface 355 of insulative body 350 such that projections 205 are directed outward from outer surface 355 in other directions as well.

According to the illustrated embodiment, projections 205 are oriented such that an extension of each, from fixed to free end, is in a proximal direction along the length of outer surface 355. Thus, the orientation of projections 205 will not impede the movement of lead 300 through a cannula, if lead 300 is implanted by pushing lead 300, with a distal end 345 of insulative body 350 leading, through the cannula, for example, having been introduced via a percutaneous axillary incision site to form the above described tunnel for the implant configuration of FIG. 1. Upon removal of the cannula, the lead may be tugged on, from a proximal end 335, to engage the exposed projections 205. However, alternate embodiments may include a filament that has some projections oriented such that the extension thereof is in a distal direction along the length of outer surface 355. In either case, lead 300 may be covered with a relatively thin removable sheath that shields the projections as the lead is passed through the cannula and tissue for implantation. In other instances, lead 300 may not be covered with the relatively thin removable sheath.

FIG. 3A illustrates insulative body 350 including a proximal segment 353, a distal segment 351, and a pre-formed bend 352 extending therebetween such that segments 353, 351 extend approximately co-planar with one another and approximately form an "L-shape". A bulk of insulative body 350 may be formed from any suitable biocompatible insulation material, such as medical grade silicone rubber or polyurethane known to those skilled in the art, and, like insulative body 150 of lead 100 (FIG. 1), insulative body 350 supports electrode circuits of lead 300, which are described below. FIGS. 3A-B further illustrate the length of outer surface 355, along which filament 200 extends, encompassing pre-formed bend 351 and distal segment 351, and filament 200 being wound about the length with an open pitch. However, in alternate embodiments, some of which are described below, the length of outer surface 355, along which filament 200 extends may be shorter, or longer, and filament 200 need not be wound. With further reference to FIGS. 3A-B, distal segment 351 of insulative body 350 has sense electrodes e1, e3 and stimulation electrode e2 mounted thereon such that electrodes e1, e2, e3 extend around a portion of the length of outer surface 355 along which filament 200 extends, and filament 200 is wound over each electrode e1, e2, e3. According to an exemplary embodiment, either end of filament 200 is secured by knotting within apertures (not shown) formed in lead 300, for example, a proximal aperture formed in the bulk of insulative body 350 in proximity to pre-formed bend 352 and a distal aperture formed within sense electrode e1 in proximity to distal end 345. Alternately, or in addition, the ends of filament 200 may be bonded to insulative body 350, by methods known to those skilled in the art, for example, by thermal, ultrasonic, or adhesive bonding, the latter with a polyurethane adhesive, if body 350 is formed from polyurethane.

Elongate electrically isolated conductors (not shown) extend within insulative body 350 of lead 300, each coupling a corresponding electrode e1, e2, e3 to a corresponding lead contact c1, c2, c3 to form the aforementioned electrode circuits. With reference to FIG. 1, in conjunction with FIG. 3A, contacts c1, c2, c3 are mounted around proximal end 335 of proximal segment 353 of body 350 to form a lead connector, which may be configured to mate with the bore of connector module 15 for electrical coupling with the contacts of device 10, according to constructions and methods known to those skilled in the art. With further reference to FIGS. 1 and 3A, the "L-shape" of insulative body 350, provided by pre-formed bend 352, conforms to the illustrated implant configuration, thereby working in conjunction with fixation projections 205 of filament 200 to help to stabilize lead 300 in the implant configuration. However, lead 300 need not include pre-formed bend 352 in some alternate embodiments. Furthermore, embodiments of the present invention are not limited to the implant configuration of FIG. 1. In other words, pre-formed bend 352 may be formed into other shapes depending on the desired implant application.

Figure 4A:
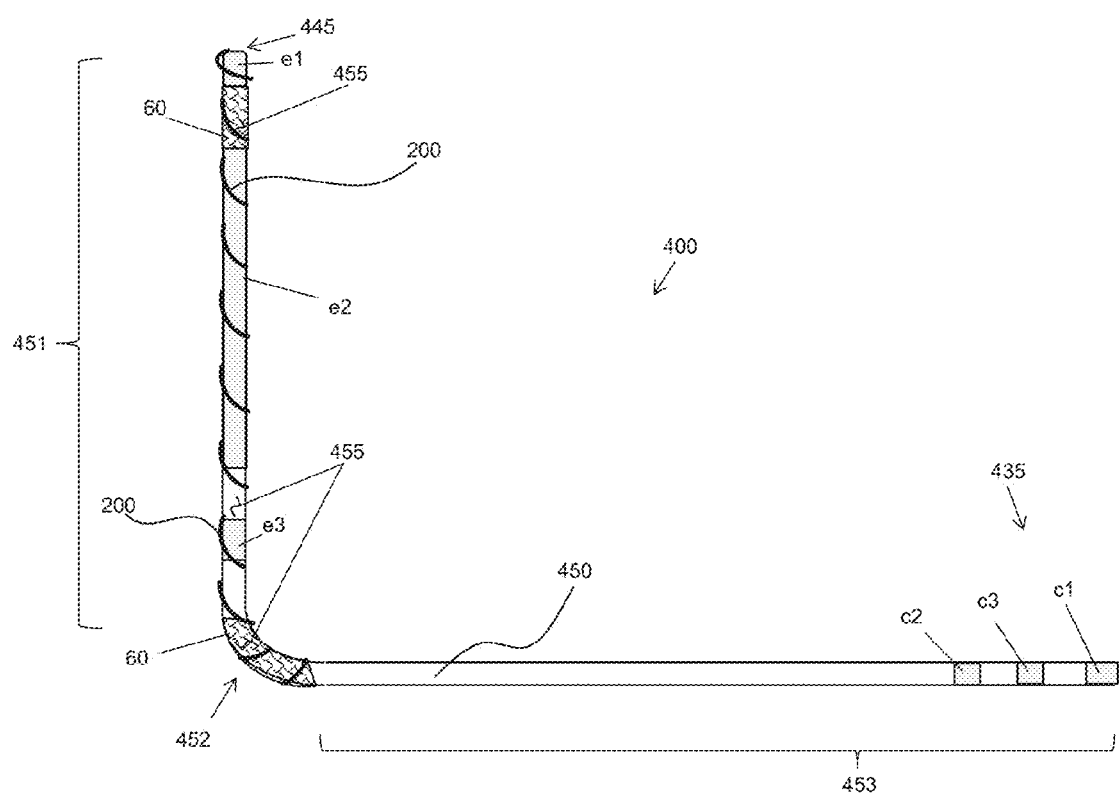
FIGS. 4A-C are plan views of alternate embodiments of an implantable medical stimulation lead including an open-work member and the filament shown in FIG. 2.

FIG. 4A is a plan view of another implantable medical stimulation lead 400, according to some alternate embodiments. FIG. 4A illustrates lead 400, like lead 300, including an insulative body 450 and non-conductive filament 200, which extends along a length of an outer surface 455 of insulative body 450, for example, being wound thereabout with an open pitch. FIG. 4A further illustrates insulative body 450 of lead 400 including an open-work member 60 forming a portion of the length of outer surface 455 along which filament 200 extends. In one example, open-work member 60 may form the portion which coincides with a pre-formed bend 452 that extends between a proximal segment 453 and a distal segment 451 of insulative body 450. In another example, open-work member 60 may located proximal to or distal to pre-formed bend 452. In instances in which lead 400 does not include pre-formed bend 452, open work member 60 may be located at a position near which lead 300 will bend during implantation.

In some instances, filament 200 may be interlaced with open-work member 60, for example, to secure filament 200 to outer surface 455. The interlacing may be accomplished by stitching filament 200 through apertures, or interstices of open-work member 60, or by braiding or weaving filament into a structure of open-work member 60 as it is initially formed. A minimum length of outer surface 455 that is formed by open-work member 60 may be approximately 0.25 inch in some embodiments, and open-work member 60 is relatively flexible and soft, or compliant, so that member 60 does not significantly increase a stiffness of insulative body 450.

Open-work member 60 may be a perforated tube (e.g., FIG. 5B), for example, formed from medical grade silicone rubber or polyurethane; alternately, open-work member 60 may be a biocompatible braided mesh or fabric woven from a plurality of monofilaments (e.g., FIG. 5A), for example, formed from polyester, polyamide, polyethylene terephthalate, or polypropylene, non-limiting examples of which include medical textiles available from Biomedical Structures and PARIETEX™, PERMACOL™, and SURGIPRO™ available from Covidien. In either case, open-work member 60 may be secured to a bulk of insulation material that forms insulative body 450, for example, polyurethane, by adhesive bonding ends of member 60 to the insulation bulk, for example, with a polyurethane adhesive, or by reflowing a portion of the bulk of insulation to embed ends of member 60 therein.

Figure 4B:
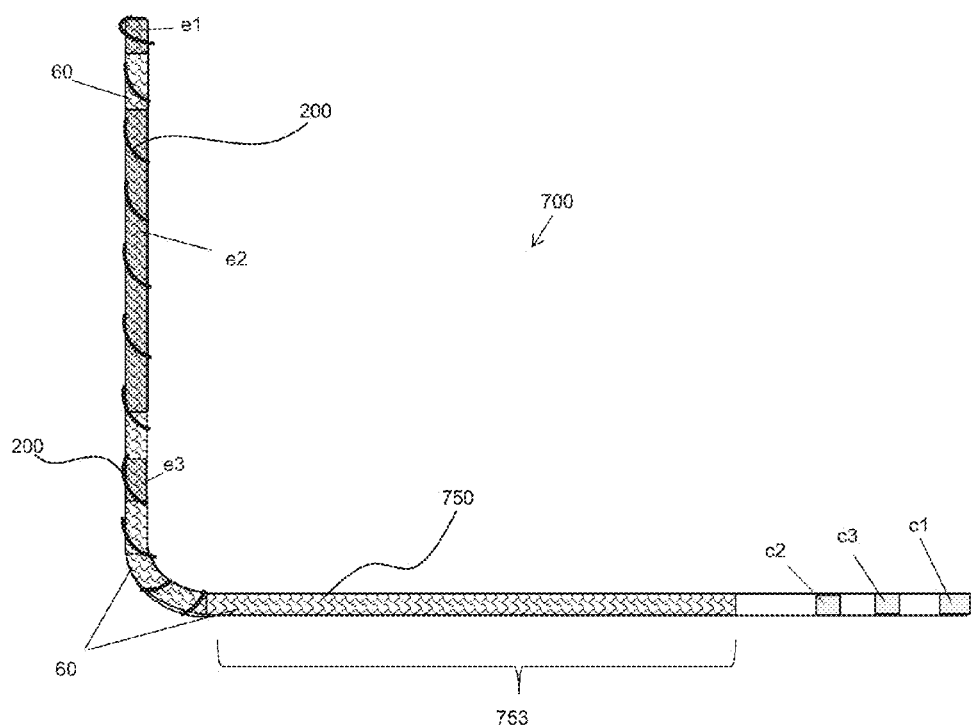

With further reference to FIG. 4A, pace/sense electrodes e1, e3 and defibrillation electrode e2 extend around another portion of the length of outer surface 455 along which filament 200 extends, filament 200 being wound over each electrode e1, e2, e3; and yet another portion of the length of insulative body 450 along which filament 200 extends is located in proximity to a distal end 445 of insulative body 450, between stimulation electrode e2 and pace/sense electrode e1, being formed by another open-work member 60. The end of filament 200 may be secured by interlacing with this other open-work member 60, and/or secured within a distal aperture formed in pace/sense electrode el in proximity to distal end 445. It should be noted that this illustrated extent of filament 200 can provide a tensile member to one or both open-work members 60 when lead 400 is pulled from proximal end 435, for example, to extract lead 400 from an implant site. FIG. 4B is a plan view of an implantable stimulation lead 700, according to some alternate embodiments, in which an insulative body 750 thereof includes a single open-work member 60. FIG. 4B illustrates open-work member 60 overlapping electrodes e1, e2, e3, so that the portion of filament 200 that is wound over electrodes e1, e2, e3 may be interlaced therewith. FIG. 4B further illustrates open-work member 60 extending proximally from filament 200, for example along a proximal length 753 of body 750 that extends into proximity with contacts c1, c2, c3. However, this proximal extent of open-work member 60 need not be included in some alternate embodiments.

Figure 4C:
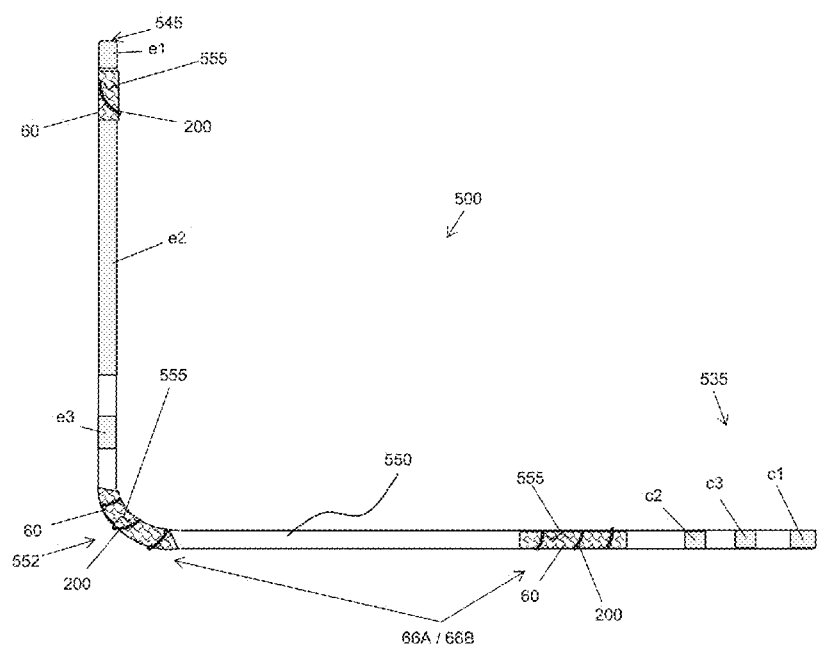

FIG. 4C is a plan view of yet another implantable medical stimulation lead 500, according to some additional embodiments. FIG. 4C illustrates a plurality of open-work members 60 forming an entirety of a length of an outer surface 555 of an elongate insulative body 550 of lead 500 over which non-conductive filament 200 extends. FIG. 4C further illustrates one open-work member 60 of lead 500 coinciding with a pre-formed bend 552 of insulative body 550, and two more open-work members 60, one being located between stimulation electrode e2 and sense electrode e1, and the other being located proximal to pre-formed bend 552, in proximity to a proximal end 535 of body 550. According to the illustrated embodiment, filament 200 is divided into separate parts, each of which is interlaced with a corresponding open-work member 60. According to some alternate embodiments that include the open-work member 60 located between electrodes e1 and e2, filament 200 need not extend between electrodes e1, e2. The proximally located member 60 of some embodiments can provide fixation, in lieu of an anchoring sleeve and sutures, for insulative body 550 of lead 500 within or adjacent to a pocket in which a device to which lead 500 is coupled is implanted, for example, device 10 in the axillary pocket illustrated in FIG. 1 when lead 500 is employed in lieu of lead 100. With reference back to FIG. 4A, it should be noted that lead 400 may also include such a proximally located open-work member 60 and a separate part of filament 200 interlaced therewith. Furthermore, with further reference to FIG. 4C, any one or two of the illustrated open-work members 60 may be employed without the other(s), according to some alternate embodiments.

Open-work member 60 is preferably biostable, or non-bioabsorbable, and interstices, or apertures, of open-work member 60 are exposed to provide spaces along outer surface 455, 555, 755 of insulative body 450, 550, 750 for tissue ingrowth when lead 400, 500, 700 is implanted, for example, subcutaneously in the configuration shown in FIG. 1 or substernally as described with respect to FIG. 1. The interstices or apertures of open-work member 60 may, for example, have a dimension on the order of 0.3 mm to 3 mm. According to some preferred embodiments, when employed in conjunction with open-work member 60, filament 200 is formed from a bioabsorbable material such as polylactic acid, polydioxanone, or a terpolymer of glycolide, dioxanone and trimethylene carbonate (e.g., the V-Loc™ 90 available from Covidien), or a copolymer of glycolic acid and trimethylene carbonate (e.g., the V-Loc™ 180 available from Covidien), or polyglycolide-poly-e-caprolactone (e.g., the Quill™ Monoderm™ available from Angiotech). Thus, when lead 400, 500, or 700 is implanted, projections 205 of filament 200, which protrude outward from the length of outer surface 455, 555, 755 engage surrounding tissue, to provide acute fixation for lead 400, 500, or 700 prior to the degradation of filament 200 and over a period of time that is sufficient for tissue ingrowth into and around open-work member 60, which ultimately provides chronic fixation for lead 400.

Figure 5A:
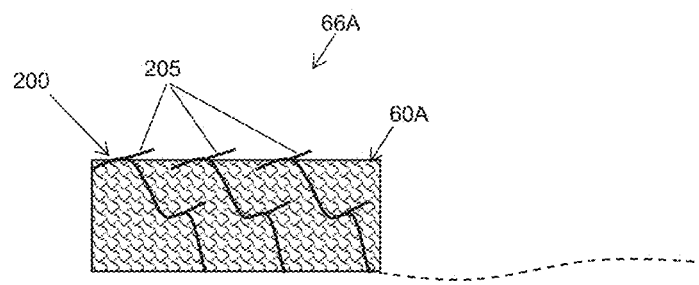
FIGS. 5A-B are a perspective view and a plan view of alternate embodiments of a fixation component for an implantable medical stimulation lead.
Figure 5B:
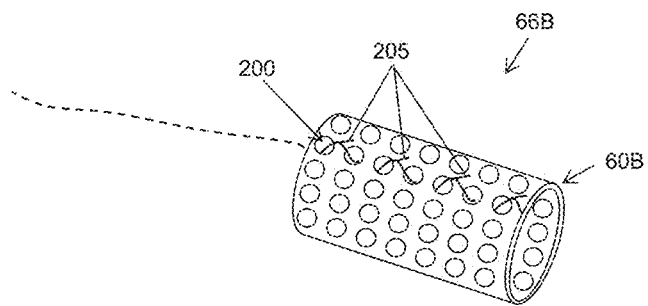

FIG. 5A is a perspective view of a component 66A, and FIG. 5B is a plan view of another component 66B, according to some alternate embodiments. Either of components 66A, 66B may be employed to form a length of an outer surface of an elongate insulative body of an implantable medical stimulation lead, for example, the length of outer surface 455, 555, 755 of body 450, 550, 750 of lead 400, 500, 700, respectively (FIGS. 4A-C). FIG. 5A illustrates component 66A including a tubular open-work member 60A, which is formed by a braided structure or a fabric woven from a plurality of monofilaments, examples of which are mentioned above.

FIG. 5B illustrates component 66B including a tubular open-work member 60B, which is formed by a perforated tube, examples of which also mentioned above. FIG. 5A further illustrates component 66A including non-conductive filament 200 interlaced with open-work member 60A, for example, either being integrally braided or woven together with the plurality of monofilaments, or being stitched through apertures, or interstices of a separately formed open-work member 60A, such that filament 200 winds, with an open pitch, around a perimeter of open-work member 60A with fixation projections 205 protruding outward from open-work member 60A. However, in alternate embodiments, filament 200 may be interlaced with open-work member 60A such that filament 200 extends along a relatively straight line, also with outward protruding projections 205, as illustrated in FIG. 5B for component 66B. Component 66B includes non-conductive filament 200 being interlaced with open-work member 60B. FIG. 5B illustrates filament 200 being interlaced with open-work member 60B such that filament 200 extends along a relatively straight line. However, in alternate embodiments, filament 200 may be interlaced such that filament 200 winds with an open pitch around a perimeter of open-work member 60B. Although not shown, open-work member 60B may include integrally formed projecting members protruding outwardly, adjacent to one or all of the apertures/perforations thereof. For example, open-work member 60B include integrally formed projecting members having been formed from portions of the wall of member 60B that are cut to form the perforations therethrough.

According to some embodiments, open-work members 60A, 60B, like open-work member 60 described above, are biostable, or non-bioabsorbable, while filament 200 that is employed therewith, is bioabsorbable, as described above in conjunction with FIGS. 4A-B. The dashed line in each of FIGS. 5A-B represents an optional length of filament 200 that extends from, and free of member 60A, 60B, according to some embodiments, for example, which may be employed by lead 300 shown in FIGS. 3A-B.

The foregoing detailed description has been described with reference to specific embodiments. However, it may be appreciated that various modifications and changes can be made without departing from the scope of the invention as set forth in the appended claims.

The invention claimed is:

1. An implantable medical therapy delivery device comprising:
    an elongate insulative body having an outer surface; and
    a non-conductive filament extending along a length of the outer surface of the insulative body, the filament including a plurality of fixation projections, the filament being secured to the outer surface of the body such that the projections protrude outward from the outer surface and are spaced apart from one another along the length of the outer surface.

2. The device of claim 1, wherein the insulative body comprises an open-work member forming at least a portion of the length of the outer surface along which the filament extends, the non-conductive filament being interlaced with the open-work member.

3. The device of claim 2, wherein the non-conductive filament comprises a bioabsorbable material.

4. The device of claim 2, wherein the insulative body includes a pre-formed bend, the bend coinciding with the open-work member.

5. The device of claim 2, wherein the open-work member forms an entirety of the length of the outer surface of the body along which the filament extends.

6. The device of claim 5, further comprising at least one electrode circuit supported by the body, and wherein the open-work member overlaps one or more electrodes of the at least one electrode circuit supported by the insulative body.

7. The device of claim 6, wherein the open-work member further forms another length of the outer surface of the insulative body, the other length extending proximally from the length of the outer surface of the body along which the filament extends.

8. The device of claim 7, wherein the insulative body includes a pre-formed bend coinciding with a portion of the length of the outer surface along which the filament extends, the pre-formed bend being located between the one or more electrodes and the other length formed by the open-work member.

9. The device of claim 2, wherein the insulative body includes a pre-formed bend, the open-work member being located proximal to the pre-formed bend.

10. The device of claim 2, wherein the open-work member comprises a plurality of open-work members.

11. The device of claim 2, further comprising at least one electrode circuit supported by the body, and wherein the open-work member forms only a portion of the length of the outer surface of the insulative body along which the filament extends, the portion of the length being located proximal to one or more electrodes of the at least one electrode circuit supported by the insulative body.

12. The device of claim 11, wherein the non-conductive filament extends distally from the portion of the length of the outer surface of the insulative body which is formed by the open-work member, the distal extent of the filament being wound with an open pitch about a remainder of the length of the outer surface of the lead body.

13. The device of claim 12, wherein at least one of the one or more electrodes extends around another portion of the length of the outer surface of the insulative body, such that at least a portion of the distal extent of the filament is wound over the electrode.

14. The device of claim 2, further comprising at least one electrode circuit supported by the body, and wherein the open-work member comprises a first open-work member, and further comprising a second open-work member, the first and second open-work members forming a first portion and a second portion, respectively, of the length of the outer surface of the body along which the filament extends, the first portion being located proximal to one or more electrodes of the at least one electrode circuit, the second portion being located distal to at least one of the one or more electrodes, and the filament being interlaced with the second open-work member.

15. The device of claim 14, wherein the insulative body includes a pre-formed bend, the bend coinciding with the first open-work member.

16. The device of claim 2, wherein the open-work member comprises a perforated tube.

17. The device of claim 2, wherein the open-work member comprises one of: a braided tubular mesh structure and a fabric woven from a plurality of monofilaments.

18. The device of claim 1, wherein the non-conductive filament is wound about the length of the outer surface of the insulative body with an open pitch.

19. The device of claim 18, further comprising at least one electrode circuit supported by the body, and wherein the length of the outer surface extends from a first location, proximal to one or more electrodes of the at least one electrode circuit supported by the insulative body, to a second location in proximity to a distal end of the insulative body.

20. The device of claim 19, wherein the insulative body includes a pre-formed bend, the bend coinciding with the first location from which the length of the outer surface extends.

* * * * *